United States Patent [19]

Mittleman

[11] 4,027,842

[45] June 7, 1977

[54] FLEXIBLE HANGER MEMBER FOR DRAINAGE BAGS AND THE LIKE

[75] Inventor: Herbert Mittleman, Deerfield, Ill.

[73] Assignee: Baxter Travenol Laboratories, Inc., Deerfield, Ill.

[22] Filed: Sept. 24, 1975

[21] Appl. No.: 616,218

[52] U.S. Cl. .................................. 248/75; 248/95; 248/215; 248/318; 128/275

[51] Int. Cl.² ........................................ F16M 13/00

[58] Field of Search ............. 128/275; 248/95, 215, 248/318, 79, 75

[56] References Cited

UNITED STATES PATENTS

| | | | |
|---|---|---|---|
| 1,123,361 | 1/1915 | Pease | 248/79 X |
| 1,333,692 | 3/1920 | Wester | 248/215 UX |
| 2,823,004 | 2/1958 | Melloh | 248/215 |
| 3,251,069 | 5/1966 | Clark | 128/275 X |
| 3,312,221 | 4/1967 | Overment | 128/275 |
| 3,529,598 | 9/1970 | Waldman | 128/275 |
| 3,599,918 | 8/1971 | Patchett | 248/215 |
| 3,630,475 | 12/1971 | Barry | 248/215 |
| 3,854,689 | 12/1974 | Engels | 248/340 |

Primary Examiner—William H. Schultz
Attorney, Agent, or Firm—Garrettson Ellis; Paul C. Flattery

[57] ABSTRACT

A flexible plastic hanger member for drainage bags and the like is provided comprising a body disposed in a plane; a hook for suspending the bag from one end of the body, means for engaging a hanger support extending from the body, and a holding part for supporting a portion of a length of tubing in transverse relation to the hanger support engaging means, the holding part including a flange member which is wider than said body for grasping the tubing, thus reducing the amount of kinking of the tubing, when compared with prior art structures. The hanger support engaging means is in acute angle relation to the hanger body for improved, resilient gripping of a hanger support.

6 Claims, 4 Drawing Figures

FLEXIBLE HANGER MEMBER FOR DRAINAGE BAGS AND THE LIKE

BACKGROUND OF THE INVENTION

In U.S. Pat. No. 3,529,598, a urine drainage bag support member is disclosed, being made of a single bent wire having a vertical body, with hooks at both ends thereof. An inlet tube retaining portion is positioned at an upper end of the hanger, in which the bent wire is proportioned to form a tube-holding eye, communicating with a throat defined by the bent wire, to allow sliding of the flexible tubing through the throat into the eye.

This structure has been used extensively in conjunction with urinary drainage bags with success, but certain disadvantages have existed.

The tube-holding eye portion of the bent wire of the prior art has, on occasions, tended to cause the tubing to kink, restricting fluid flow through the tubing. When this happens, the nurse must readjust the arrangement of the tubing in the eye carefully, so as to avoid such kinking.

As a further disadvantage, while the structure of the prior art hangs effectively on rectangular bed rails and the like, its performance is not as desirable on cylindrical bed rails, as are found on modern hospital beds, particularly when the bed is in elevated position and the cylindrical rail not horizontal. In that case, sometimes the prior art bag hanger tends to slide.

Also, when a patient using a drainage bag is ambulatory, he desires to hang the bag on a chair leg brace or the like. The prior art hanger structure is inconvenient for that purpose, being often prone to falling off.

The improved hanger of this invention for urinary drainage bags and the like is preferably a somewhat-resilient, plastic structure, in which the hanger member defines an acute angle to the general axis of the body of the hanger structure. This, coupled with the resilience of the structure, provides a hanger structure which can grip under tension a cylindrical bed rail or another structure as desired, thus holding the drainage bag in vertical position, without danger of falling off and with less possiblity of undesirable sliding along the rail.

Furthermore, the tube retaining eye defined by the structure of this invention includes an enlarged flange, providing an enlarged flange surface area to grip the tubing which is retained therein. Accordingly, kinking of the tubing, and the resultant blockage of flow, is greatly reduced.

The hanger members of this invention are also less expensive than their prior art metal counterparts, and eliminate the need for rubber end tips that have been utilized on the commercial version of the prior metal structures, to avoid tearing bags and packaging by the ends of the wire rods from which the prior art hangers were made.

DESCRIPTION OF THE INVENTION

The bag hanger of this invention comprises a preferably-resilient plastic structure including an elongated body, a hook for suspending a bag or the like from one end of the body, means extending from the body for engaging a hanger support, and, generally, a holding part for supporting a portion of the length of tubing in transverse relation to the hanger support engaging means.

In accordance with this invention, the holding part defines an eye portion defined by a flange for retaining and holding the tubing of a bag. The flange is wider than the body, being typically at least five mm. in width, and preferably about one centimeter in width, to reduce kinking in the tubing retained by such flange.

Furthermore, the engaging means for the hanger support preferably comprises an elongated portion which defines an acute angle to the body of the hanger member. Accordingly, the resulting structure, particularly when resilient, serves as gripping member for cylindrical bed rails, door handles, chair arms, and the like, for positive grasping engagement of a structure from which the hanger is to be supported.

In the drawings, FIG. 1 is a perspective view of one type of hanger of this invention, carrying a conventional hospital urinary drainage bag with inlet tubing, and affixed to a horizontal, cylindrical rail such as a bed rail.

Figure 1:
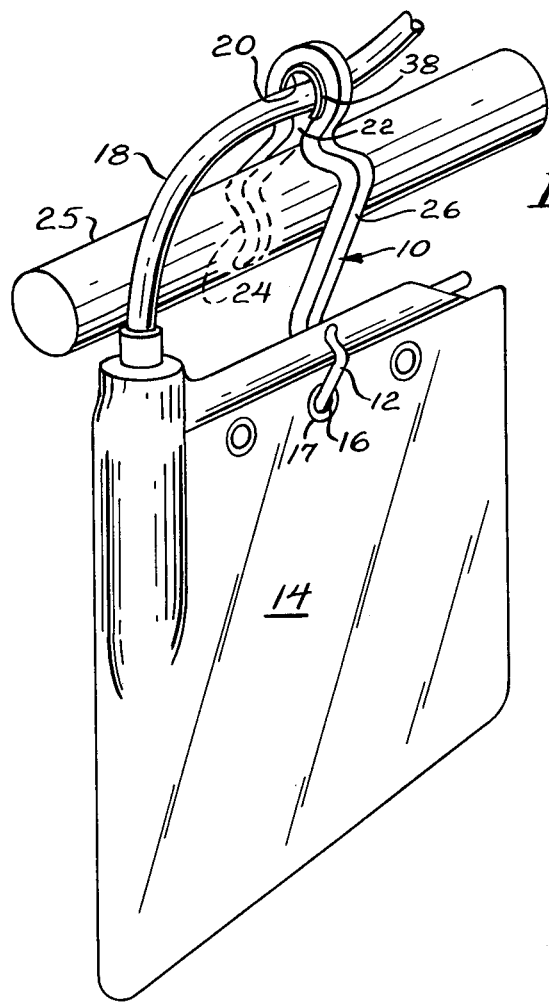

Referring to the drawings, and especially FIG. 1, a hanger 10 is shown defining a hook 12 at one end thereof for supporting of a urinary drainage bag 14 through a hole 16 in the bag, having a heat sealed periphery 17 for sealing of the bag, or any other desired means for hanging the bag from hook 12.

Inlet tubing 18 of bag 14 is shown to be positioned within the portion of hanger 10 which defines eye 20. Tube 18 can be placed into eye 20 by passing it through throat portion 22 defined in hanger 10.

Hanger support engaging means 24 is shown to be positioned upon a hanger support such as cylindrical structure 25, for example, a bed rail. If bed rail 25 is somewhat larger than the space between support engaging means 24 and the body 26 of hanger 10, the resilient hanger may stretch outwardly as shown in phantom lines in FIG. 2, to accomodate the bed rail or the like. This provides the additional advantage of a spring-biased tension between hanger 10 and bed rail 25, tending to hold the hanger in position.

Figure 2:
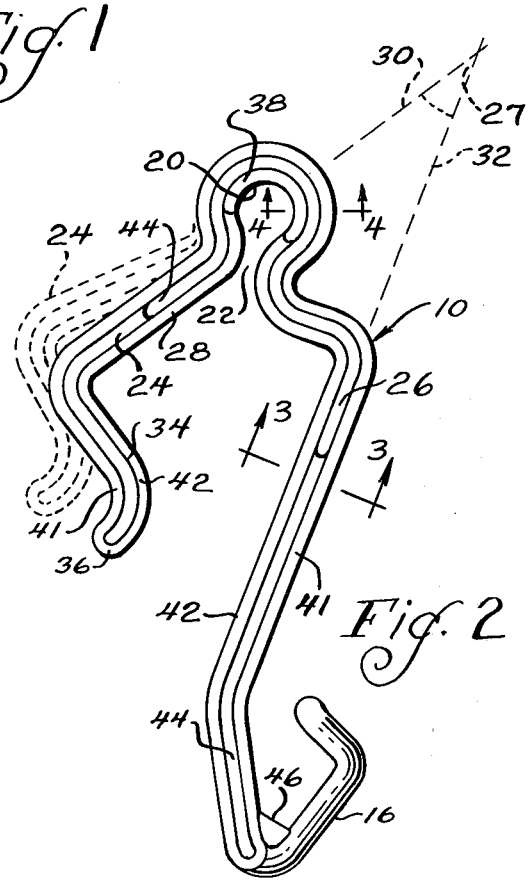
FIG. 2 is an enlarged, elevational view of the hanger support of this invention shown in FIG. 1.
Figure 3:
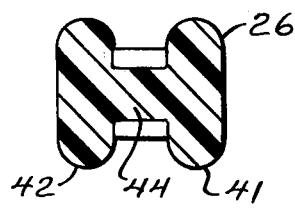
FIG. 3 is a sectional view taken along line 3—3 of FIG. 2.

Engaging means 24 comprises an elongated portion 28, that defines an acute angle 27 with respect to body 26, as clearly shown in FIG. 2 by the phantom linear extensions 30, 32 of elongated member 28 and body 26 respectively. Preferably angle 27 is no more than about 45° when member 28 is in its unbiased position. This acute angular relationship assists in providing a more stable, gripping retention of a support for the hanger and the drainage bag carried therewith.

Inwardly turning portion 34 at the free end of elongated member 28 points toward body 26, and provides added stability to the hanging of the structure 10, while terminal, outwardly-turning portion 36, at the free end of portion 34, simplifies the insertion of bed rail 25 or the like between members 24 and 26.

Tubing retention eye 20 is largely defined by an inner, enlarged flange poriton 38, integral with the remainder of hanger 10. This enlarged flange portion preferably has a width 40 of about 1 centimeter (FIG. 4), thus providing a greatly enlarged surface area for gripping tubing 18, and retaining it in non-kinking manner, when compared with the narrower, bent wire structure of U.S. Pat. No 3,529,598. That wire structure may have a zone of tubing contact at its corresponding eye portion of only about two mm. in width, and accordingly is more likely to kink tubing, with resultant flow blockage.

Figure 4:
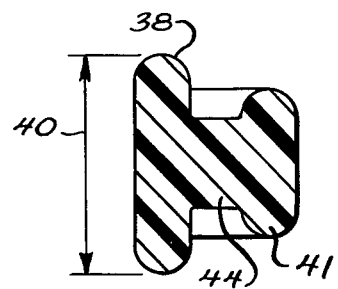
FIG. 4 is a sectional view taken along line 4—4 of FIG. 2.

With the exception of hook 16, the hanger of this invention may preferably define a generally H-shaped cross-section comprising a pair of lateral members 41, 42, connected by transverse member 44. As shown in FIGS. 2 and 4, lateral member 42 is interrupted by enlarged flange 38. Lateral member 42 is integral with flange 38.

The cross-sectional structure utilized in the hanger of this invention provides improved strength with the use of less plastic material. Typically, polystyrene, polyethylene, or any other desired thermoplastic material can be used to manufacture the hanger of this invention.

Web 46 may be conveniently placed at the bottom of hook portion 16, as shown in FIG. 2, to strengthen hook 16 for holding a large, fluid-filled bag and the like.

The hanger of this invention accordingly provides a less expensive structure which does not kink fluid flow tubes passing through its eye portion as easily as the prior art structures, and which provide an improved hanging structure capable of gripping a cylindrical bed rail or the like for more secure hanging. This results in less danger of falling off and spilling of the bag on the floor.

It is also contemplated that the hanger of this invention can be used for hanging other devices besides those specified herein.

The above has been offered for illustrative purposes only, and is not to be viewed as limiting the invention of this application, which is as defined in the claims below.

That which is claimed is:

1. A hangar for a drainage bag or the like which comprises: an elongated body, bag suspending means at one end of said body, means for engaging a hangar support, said means being carried at the other end of said body, and a holding part for supporting a portion of a length of tubing in transverse relation to said hangar support engaging means, the improvement comprising, said holding part including a flange of greater width than said body, said flange defining an eye portion for receiving and holding said tubing for the prevention of kinking thereof, said hangar support engaging means comprising an elongated member defining an acute angle of no more than substantially 45° to said body, for added hanging stability, said hangar being resilient, for improved gripping retention of a hanger support.

2. The hanger of claim 1 in which the width of said flange is at least five millimeters.

3. The hanger of claim 1 in which said elongated member defines, at a free end thereof, an inwardly turning portion, pointing toward said body, for added hanging stability.

4. The hanger of claim 3 in which said inwardly turning portion defines, at a free end thereof, an outwardly turning portion to facilitate the insertion of a hanger support between said elongated member and said body.

5. The hanger of claim 4 in which said flange has a width of about one centimeter.

6. The hanger of claim 5 in which the major portion of said hanger is of H-shaped cross-sectional construction.

* * * * *